United States Patent

Andersson et al.

Patent Number: 5,214,156
Date of Patent: May 25, 1993

[54] THERAPEUTICALLY USEFUL TETRALIN DERIVATIVES

[75] Inventors: Bengt R. Andersson, Lindome; Per Arvid E. Carlsson, Goteborg; Kjell A. I. Svensson, Alingas; Hakan V. Wikstrom, Partille, all of Sweden

[73] Assignee: The Upjohn Company, Kalamazoo, Mich.

[21] Appl. No.: 866,391

[22] Filed: Apr. 10, 1992

Related U.S. Application Data

[60] Division of Ser. No. 784,609, Oct. 29, 1991, abandoned, which is a continuation of Ser. No. 571,561, Aug. 30, 1990, abandoned, which is a continuation-in-part of Ser. No. 173,130, Mar. 25, 1988, abandoned.

[51] Int. Cl.$^5$ .................... C07P 333/20; A61K 31/38; A61K 31/135; C07C 211/00
[52] U.S. Cl. ....................... 549/75; 514/438; 514/654; 514/657; 564/374; 564/382; 564/428
[58] Field of Search ......... 514/654, 657, 438; 564/374, 382, 428; 549/75

[56] References Cited

U.S. PATENT DOCUMENTS 3,253,037  5/1966  Huebner ................ 260/577
4,564,628  1/1986  Horn .................... 549/75

FOREIGN PATENT DOCUMENTS 0168505  1/1986  European Pat. Off. .
0272534  6/1988  European Pat. Off. .
1377356  12/1974  Japan .
1597140  9/1981  United Kingdom .

OTHER PUBLICATIONS

Wikstrom, H. et al., "Conformational Analysis of 2-Aminoindans and 2-(Aminomethyl)indans in Relation to Their Central Dopaminergic Effects and a Dynamic Dopamine Receptor Concept," J. Med. Chem. 30(7):1115-20 (1987).
Cannon, J. G. et al., "Conformationally Restricted Congeners of Dopamine Derived from 2-Aminoindan," J. Med. Chem. 25:1442-46 (1982).
Dren, A. T. et al., "Local Anesthetic Activity and Primary Examiner—Allen J. Robinson
Assistant Examiner—Peter G. O'Sullivan
Attorney, Agent, or Firm—Donald Corneglio

[57] ABSTRACT

This invention is therapeutically useful tetralins and pharmaceutically acceptable acid addition salts thereof of the formula (List continued on next page.)

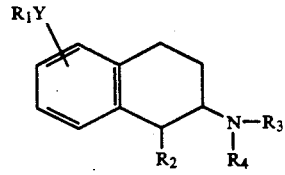

wherein
$YR_1$ is $OR_1$ at the 8 position where $R_1$ is $-CH_2-(C_{3-8}$ cycloalkyl);
$R_2$ is hydrogen or $C_{1-3}$ alkyl;
$R_3$ is $-CH_2-(C_{3-8}$ cycloalkyl);
$R_4$ is hydrogen, $C_{1-8}$ alkyl, $-CH_2-(C_{3-4}$ cycloalkyl), $-(CH_2)_m-R_5$ or $-CH_2-CH_2-X-(CH_2)_nCH_3$; n is zero to 3 and m is 2 or 3; X is oxygen or sulfur;
$R_5$ is phenyl, $C_{1-3}$ alkoxy, $C_{1-3}$ alkyl, 2-thiophene, 3-thiophene, or phenyl substituted with one or two substituent groups selected from chlorine, bromine or fluorine; and with the proviso that when $R_3$ contains more than four carbon atoms and $R_4$ is alkyl, said alkyl contains from 1 to 3 carbon atoms.

Alternatively, $-YR_1$ is $-S-(C_{1-3}$ alkyl) at the 5, 6, 7 or 8 position of the aromatic ring or $OR_1$ at the 8 position where $R_1$ is selected from the group consisting of $C_{1-8}$ alkyl, $C_{2-8}$ alkenyl, $-CH_2-(C_{3-8}$ cycloalkyl) or benzyl;
$R_2$ is hydrogen or $(C_1-C_3)$ alkyl;
$R_3$ is $-CH_2-(C_3-C_8)$ cycloalkyl;
$R_4$ is $-(CH_2)_m-(2$-thiophenyl or 3-thiophenyl); and m is 2 or 3.

5 Claims, No Drawings

OTHER PUBLICATIONS

Acute Toxicity of N-Substituted 1,2,3,4-Tetrahydro-1- and 2-naphthylamines," J. Pharmaceutical Sciences 67(6):880-82 (1978).

Ames, D. E. et al., "The Synthesis of Alkoxy-1,2,3,4-tetrahydronaphthalene Derivatives. Part I.- 2-Amino—, Alkylamino-, and Dialkylamino-derivatives," J. Chem. Soc. 2636-41 (1965).

Arvidsson, L.-E. et al., "8-Hydroxy-2-(alkylamino)-tetralins and Related Compounds as Central 5-Hydroxytryptamine Receptor Agonists," J. Med. Chem. 27:45-51 (1984).

"Arvidsson, L.-E. et al., 8-Hydroxy-2-(di-n-propylamino)tetralin, a New Centrally Acting 5-Hydroxytryptamine Receptor Agonist," J. Med. Chem. 24:921-23 (1981).

McDermed, J. D. et al., "Synthesis and Dopaminergic Activity of (±)-, (+)-, and (−)-2-Di-propylamino-5-hydroxy-1,2,3,4-tetrahydronaphthalene," J. Med. Chem. 19(4):547-49 (1976).

McDermed, J. D. et al., "Synthesis and Pharmacology of Some 2-Aminotetralins. Dopamine Receptor Agonists," J. Med. Chem. 18(4):362-67 (1975).

Arvidsson, L.-E. et al., "(+)-c-8-Hydroxy-1-methyl-2-(di-n-proplyamino)tetralin: A Potent and Highly Stereoselective 5-Hydroxytryptamine Receptor Agonist," J. Med. Chem. 30:2105-09 (1987).

Rusterholz, D. B. and C. F. Barfknecht, "Ergoline Congeners as Potential Inhibitors of Prolactin Release," J. Med. Chem. 19(1):99-102 (1976).

Cannon, J. G. et al., "Synthesis and Dopaminergic Activity of (R)-and (S)-4-Hydroxy-2-(di-n-propylamino)indan," J. Med. Chem. 28:515-18 (1985).

Temple, D. M., "Some New Sympathomimetic Amines: N-Cycloalkyl Derivatives of 1,2,3,4-Tetrahydro-2-Naphthylamine and of Noradrenalone," Aust. J. Chem. 20:601-04 (1967).

THERAPEUTICALLY USEFUL TETRALIN DERIVATIVES

CROSS-REFERENCE TO RELATED PATENT APPLICATIONS

This application is a divisional of U.S. Ser. No. 07/784,609, filed Oct. 29, 1991, now abandoned, which was a continuation of U.S. Ser. No. 07/571,561, filed Aug. 30, 1990, abandoned, which was the national phase application of PCT/US89/00974, filed Mar. 15, 1989, which was a continuation-in-part of U.S. Ser. No. 07/173,130, filed Mar. 25, 1988, abandoned.

FIELD OF THE INVENTION

The present invention is related to new 1,2,3,4-tetrahydro-2-naphthylamines, to processes for preparing such compounds, pharmaceutical preparation of such compounds and the use of such compounds in manufacture of a pharmaceutical preparation.

BACKGROUND OF THE INVENTION

In depressed patients evidence indicates the neurotransmission in the central nervous system (CNS) may be disturbed. These disturbances involve the neurotransmitters noradrenaline (NA) and 5-hydroxytryptamine (5-HT). The drugs most frequently used in the treatment of depression are considered to act by improving the neurotransmission of either or both of these physiological agents. Available data suggests that the enhancement of 5-HT neurotransmission will primarily improve depressed mood and anxiety, whereas the enhancement of noradrenaline neurotransmission will improve retardation symptoms occurring in depressed patients. In recent years many efforts have been made to develop new drugs with high selectivity for the improvement of the 5-HT neurotransmission in the CNS.

The mechanism of action for the drugs generally used today in the therapy of mental depression is generally believed to be indirect with the drugs acting by blocking the reuptake of the neurotransmissers, NA and/or 5-HT, released from nerve terminals in the CNS, which increases the concentration of these transmitters in the synaptic cleft and restores an adequate neurotransmission. For example, the clinically documented antidepression drug, zimelidine (dimethylamino-1-(4-bromophenyl)-1-(3-pyridyl)propene) acts as such a reuptake inhibitor with high selectivity for 5-HT neurons.

A fundamentally different way to improve the neurotransmission in the central 5-HT neurons would be to use a 5-HT receptor agonist acting directly upon the 5-HT receptors, and particularly the 5-HT$_{1A}$ receptor. In order to minimize undesired side effects, a high selectivity for this kind of receptor would be necessary.

Clinically, 5-HT$_{1A}$ agonists have also demonstrated anxiolytic properties. The drug, Buspirone, is the only currently available marketed 5-HT$_{1A}$ agonist having anxiolytic activity. This compound antagonizes dopamine receptors at the same dose it stimulates 5-HT$_{1A}$ receptors. A similar drug, Gepirone, also has dopamine antagonist properties. These dopamine antagonist properties reduce the clinical utility of these compounds however because long term treatment with dopamine antagonists can produce tardive dyskinesia.

The search for new CNS active compounds is focused on finding compounds with selective 5-HT$_{1A}$ receptor agonist effects without detrimentally influencing central dopamine receptors.

Drugs acting on central dopamine transmission are clinically effective in treating a variety of central nervous system disorders such as parkinsonism, schizophrenia, and mano-depressive illness. In parkinsonism, for example, the nigro-neostriatal hypofunction can be restored by an increase in postsynaptic dopamine receptor stimulation. In schizophrenia, the condition can be normalized by achieving a decrease in postsynaptic dopamine receptor stimulation. Classical antipsychotic agents directly block the postsynaptic dopamine receptor. The same effect can be achieved by inhibition of intraneuronal presynaptic events essential for the maintenance of adequate neurotransmission, transport mechanism and transmitter synthesis.

In recent years a large body of pharmacological, biochemical and electrophysical evidence has provided considerable support in favor of the existence of a specific population of central autoregulatory dopamine receptors located in the dopaminergic neuron itself. These receptors are part of a homeostatic mechanism that modulates nerve impulse flow and transmitter synthesis and regulates the amount of dopamine released from the nerve endings.

Direct dopamine receptor agonists, like apomorphine, are able to activate the dopamine autoreceptors as well as the post synaptic dopamine receptors. The effects of autoreceptor stimulation appear to predominate when apomorphine is administered at low doses, whereas at higher doses the attenuation of dopamine transmission is outweighed by the enhancement of postsynaptic receptor stimulation. The antipsychotic and antidyskinetic effects in man of low doses of apomorphine are likely due to the autoreceptor-stimulator properties of this dopamine receptor agonist. This body of knowledge indicates dopamine receptor stimulants with a high selectivity for central nervous dopamine autoreceptors would be valuable in treating psychiatric disorders.

INFORMATION DISCLOSURE STATEMENT

The following documents could be important in the examination of this application.

Derwent 12191K (Belgium 893,917) discloses indanyl substituted imidazole derivatives and tetralyl imidazole derivatives wherein the aromatic ring of the indanyl and tetralyl groups may be substituted with various groups including halogen, alkyl (C$_1$–C$_6$, trihaloalkyl, alkoxy and alkylthio. The compounds are useful in treating atherosclerosis.

British Patent 1,377,356 discloses 8-hydroxy and 8-methoxy substituted-1,1-dialkyl-2-aminotetralins wherein the amino group is unsubstituted or substituted with an alkyl C$_1$–C$_6$. These compounds are useful as analgesics.

Derwent 40378A/23 (British 1,597,140) discloses, among other compounds, 2-aminotetralins substituted on the aromatic ring with halogen, di-chloro and additionally hydroxy or an alkanoyloxy group. These compounds are useful in treating heart conditions and/or Parkinson's disease.

Switzerland 637,363 (Derwent 729,386) and Switzerland 637,364 discloses, among other compounds, 2-aminotetralins substituted on the aromatic ring with halogen, di-chloro and additionally hydroxy, alkyl or other functional groups. These compounds are stimulants of α- and β-adrenergic and dopamine receptors rendering them useful in treating heart failure, cardiac infarct, hypertension and Parkinson's disease.

Germany 2,333,847 (Derwent 7633V) discloses a very broad scope of compounds which can include amino tetralins and amino indanes substituted on the aromatic ring with alkoxy or halogen and additionally hydroxy, aralkyloxy or acyloxy. These compounds are water softening agents and corrosion inhibitors in lubricants as well as CNS-depressants and anti-arrhythmics.

European 272,534-A (Derwent) discloses 2-aminotetralins substituted in the 8-position by halogen (fluorine, chlorine, bromine or iodine) among many other compounds within a broad disclosure. These compounds are useful serotonin antagonists or agonists with high affinity for cerebral 5-HT[1] receptors rendering them useful in the treatment of CNS disorders, cognitive deficiencies, Alzheimer's disease, cardiovascular disorders, pain and intestinal disorders.

German 2803582 (Derwent 58247B) discloses 2-aminotetralins wherein the amino group is substituted with inter alia alkyl, or cycloalkyl and wherein the aromatic ring is substituted with inter alia alkyl, halogen, di-chloro and additionally with hydroxy or an alkanoyloxy group. These compounds have a stimulant effect on α- and β-adrenoreceptors and on dopamine receptors and are useful in the treatment of heart failure, cardiac infarct, elevated blood pressure and Parkinson's disease.

Wikstrom, H., et al., J. Med. Chem. 30, 1115 (1987) discloses 4-hydroxy-and 4-methoxy-2-aminoindanes wherein the amino moiety is unsubstituted or is substituted with dimethyl or di-n-propyl; 5-hydroxy-2-dimethylaminoindane; and 7-hydroxy-2-aminotetralin wherein the amino moiety is substituted with dimethyl or di-n-propyl. This paper focuses on the conformational analysis of the compounds in relation to their central dopaminergic effects.

J. G. Canon, et al., J. Med. Chem. 25, 1442-1446 (1982) and J. Med. Chem. 28, 515-518 (1985) disclose inter alia, 4-hydroxy- and 5-hydroxy-2-di-n-propylindane in a study dealing with the conformational analysis of a series of 2-aminoindans.

Seeman, et al., Molecular Pharmacology 28, 291-299 (1985) includes a number of known hydroxy substituted and methoxy substituted aminotetralins and aminoindans in a $D_2$ receptor binding affinity study.

A. T. Dren, et al., J. Pharm. Sci. 67, 880-882 (1978) discloses among other compounds 2-aminotetralin wherein the amino group is mono-substituted with cyclopropylmethyl or cyclopropyl and the aromatic ring is substituted with methoxy at the 5- or 6-position. These compounds were tested for local anesthetic activity.

D. E. Ames, et al., J. Chem. Soc. 2636 (1965) describes the synthesis of various di-alkoxy substituted aminotetralins wherein the alkoxy groups have from 1 to 4 carbon atoms. 6-Methoxy-2-aminotetralin is also described.

L. E. Arvidsson, J. Med. Chem. 27, 45-51 (1984) describes a series of 2-aminotetralins wherein the amine is substituted with one or two lower alkyl groups of 1-4 carbon atoms, octyl or benzyl, and the aromatic ring is substituted 5- and/or 8-position with hydroxy or lower alkoxy. These compounds were tested as dopamine and 5hydroxytryptamine receptor agonists.

L. E. Arvidsson, et al., J. Med. Chem. 24, 921-923 (1981) discloses 8-methoxy-2-aminotetralins wherein the amino moiety is substituted with n-propyl, benzyl or di-n-propyl and 2di-n-propylaminotetralins wherein the aromatic ring is substituted in the 5-, 6-, 7- or 8-position with hydroxy. These compounds were evaluated for their affect on dopaminergic and α-adrenergic receptors.

J. D. McDermed, et al., J. Med. Chem. 19, 547-549 (1976) discloses 5,6-dihydroxy and 5-, 6- and 7-hydroxy-2-di-n-propylaminotetralins in a study of their dopaminergic activity.

J. D. McDermed, et al., J. Med. Chem. 18, 362-367 (1975) discloses a large series of 2-aminotetralins wherein the aromatic ring is mono- or di-substituted with hydroxy, methyl or lower alkoxy and the amine moiety is unsubstituted or substituted with lower alkyl, benzyl, alkoxyalkyl or forms part of a monocyclic heterocyclic group. These compounds were evaluated for their dopaminergic activity.

L. E. Arvidsson, J. Med. Chem. 30, 2105-2109 (1987) evaluates the 5-HT receptor agonist activity of 1-methyl-2-di-n-propylaminotetralins substituted in the 8-position with hydroxy or methoxy.

D. B. Rusterholz, et al., J. Med. Chem. 19, 99-102 (1976) discloses 5- and/or 8-substituted-2-aminotetralins wherein the 5-or 8-position is substituted with methyl, hydroxy or methoxy. The effect of these compounds on prolactin release is evaluated.

J. G. Cannon, et al., J. Med. Chem. 28, 515 (1985) describes the resolution of 4-hydroxy-2-(di-n-propyl)aminoindane, a synthetic precursor to a potent dopaminergic agonist.

SUMMARY OF THE INVENTION

This invention encompasses compounds of Formula I and pharmaceutically acceptable acid addition salts thereof, wherein —$YR_1$ is one substituent on the 5, 6, 7 or 8 position of the aromatic ring and is —$S_{(1-C_3)}$alkyl or —$OR_1$ wherein $R_1$ is selected from the group consisting of ($C_1$-$C_8$) alkyl, ($C_1$-$C_8$) alkenyl, —$CH_2$—($C_3$-$C_8$) cycloalkyl or benzyl; wherein $R_2$ is hydrogen or ($C_1$-$C_3$) alkyl; wherein $R_3$ is —$CH_2$—($C_3$-$C_8$) cycloalkyl; wherein $R_4$ is hydrogen, ($C_1$-$C_8$) alkyl, —$CH_2$—($C_3$-$C_4$) cycloalkyl, —$(CH_2)_m$—$R_5$ or —$CH_2CH_2$—$X$—$(CH_2)_n CH_3$; wherein n is zero to 3 and m is 2 or 3; wherein X is oxygen or sulfur; and wherein $R_5$ is phenyl; phenyl substituted with one or two substituent groups selected from chlorine, bromine, fluorine, ($C_1$-$C_3$)alkoxy, or ($C_1$-$C_3$)alkyl; 2-thiophene; or 3-thiophene; with the proviso that when $R_3$ contains more than 4 carbon atoms and $R_4$ is alkyl said alkyl contains from one to 3 carbon atoms.

The compounds of this invention possess selective pharmacological properties and are useful in treating central nervous system disorders including antidepression symptoms, anxiolytic symptoms, panic attacks, obsessive-compulsive disturbances, senile dementia, emotional disturbances related to dementia disorders, and stimulation of sexual activity. The compounds of this invention are also useful to alleviate aggressive behavior, confusional delirious states and impotence. Certain compounds of this invention additionally possess blood pressure lowering affects. Processes for preparation of these compounds, their pharmaceutical use and pharmaceutical preparations employing such compounds constitute further aspects of the invention.

According to a preferred embodiment the invention is related to compounds of Formula I wherein $R_3$ is —$CH_2$—($C_3$-$C_8$) cycloalkyl, $R_4$ is ($C_1$-$C_8$) alkyl or —$CH_2$—($C_3$-$C_4$) cycloalkyl and $R_1$ is a methyl group.

A more preferred embodiment are compounds of Formula I wherein $R_3$ is cyclopropylmethyl, $R_4$ is ($C_1$-$C_4$) alkyl or cyclopropylmethyl and $R_1$ is a methyl group.

An object of the invention is to provide compounds for therapeutic use, especially compounds having a therapeutic activity in the central nervous system. Another object is to provide compounds having an effect on the 5-HT$_{1A}$ receptor in mammals including man. A further object of this invention is to provide compounds having an effect on the subclass of dopamine receptors known as the $D_2$ receptor.

DETAILED DESCRIPTION OF THE INVENTION

The compounds of this invention are identified in two ways: by the descriptive name and reference to labelled structures contained in appropriate charts. In appropriate situations, the proper stereochemistry is also represented in the charts.

In this document the parenthetical term ($C_n$—$C_m$) is inclusive such that a compound of ($C_1$-$C_8$) would include compounds of one to 8 carbons and their isomeric forms. The various carbon moieties are defined as follows: Alkyl refers to an aliphatic hydrocarbon radical and includes branched or unbranched forms such as methyl, ethyl, n-propyl, isopropyl, n-butyl, isobutyl, sec-butyl, t-butyl, n-pentyl, isopentyl, neo-pentyl, n-hexyl, isohexyl, n-heptyl, isoheptyl, and n-octyl.

Alkoxy as represented by —$OR_1$ when $R_1$ is ($C_1$-$C_8$) alkyl refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, t-butoxy, n-pentoxy, isopentoxy, neo-pentoxy, n-hexoxy, isohexoxy, n-heptoxy, isoheptoxy, and n-octoxy.

Alkenyl refers to a radical of an aliphatic unsaturated hydrocarbons having a double bond and includes both branched and unbranched forms such as ethenyl, 1-methyl-1-ethenyl, 1-propenyl, 2-propenyl, 1-butenyl, 2-butenyl, 3-butenyl, 2-methyl-1-butenyl, 1-pentenyl, 2-pentenyl, 3-pentenyl, 4-pentenyl, 1-methyl-4-pentenyl, 3-methyl-1-pentenyl, 3-methyl-2-pentenyl, 1-hexenyl, 2-hexenyl, 3-hexenyl, 4-hexenyl, 1-methyl-4-hexenyl, 3-methyl-1hexenyl, 3-methyl-2-hexenyl, 1-heptenyl, 2-heptenyl, 3-heptenyl, 4-heptenyl, 1-methyl-4-heptenyl, 3-methyl-1-heptenyl, 3-methyl-2-heptenyl, 1-octenyl, 2-octenyl, or 3-octenyl. Cycloalkyl refers to a radical of a saturated cyclic hydrocarbon such as cyclopropyl, cyclobutyl, cyclopentyl, cyclohexyl, cycloheptyl, or cyclooctyl.

It will be apparent to those skilled in the art that compounds of this invention may contain chiral centers. The scope of this invention includes all enantiomeric or diastereomeric forms of Formula I compounds either in pure form or as mixtures of enantiomers or diastereomers. The compounds of Formula I contain two asymmetric carbon atoms in the aliphatic ring moiety, including the ring carbon atoms adjacent to the nitrogen atom. The therapeutic properties of the compounds may to a greater or lesser degree depend on the stereochemistry of a particular compound. Pure enantiomers as well as enantiomeric or diastereomeric mixtures are within the scope of the invention.

Both organic and inorganic acids can be employed to form non-toxic pharmaceutically acceptable acid addition salts of the compounds of this invention. Illustrative acids are sulfuric, nitric, phosphoric, hydrochloric, citric, acetic, lactic, tartaric, palmoic, ethanedisulfonic, sulfamic, succinic, cyclohexylsulfamic, fumaric, maleic, and benzoic acid. These salts are readily prepared by methods known in the art.

The compounds of this invention may be obtained by one of the following methods described below and outlined in the appropriate charts. A compound of the formula, C-1, may be converted into a compound of Formula I, when $R_1$ and $R_4$ are the same, by alkylation of the nitrogen and oxygen atoms with an appropriate alkylating agent. The compound of the formula, C-1, may be treated with an alkyl-halide or tosylate of the formula $R_aX$, when $R_a$ is alkyl or cycloalkyl, and when X is Cl, Br, I or TsO, in an organic solvent such as acetonitrile or acetone and in the presence of a base such as potassium carbonate or sodium hydroxide.

Alternatively, the compounds of this invention may be obtained from a compound of the formula, C-2, by alkylation of the hydroxy moiety with an appropriate alkylating agent. The starting compound, C-2, may be treated with an alkyl halide or tosylate $R_bX$, when $R_b$ is alkyl, alkenyl, cycloalkyl, or benzyl, when X is Cl, Br, I or TsO, in an organic solvent such as acetonitrile or acetone and in the presence of a base such as potassium carbonate or sodium hydroxide.

In addition, a compound of the formula, C-3, may be converted into a compound of Formula I, by alkylation of the nitrogen atom with an appropriate alkylating agent. The starting compound may be treated with an alkyl halide or tosylate $R_cX$, when $R_c$ is alkyl, cycloalkyl, heterocyclic alkyl, ethylalkoxy or ethylthiaalkyl, when X is Cl, Br, I or TsO, in an organic solvent such as acetonitrile or acetone and in the presence of a base such as potassium carbonate or sodium hydroxide, or the starting compound, C-3, may be treated with a carboxylic acid sodium borohydride complex, when the carboxylic acid is HOOC—($C_1$-$C_7$)alkyl, HOOC—($C_3$-$C_8$)cycloalkyl, HOOC—$(CH_2)_p$—$R_5$, or HOOC—$CH_2$—X—$(CH_2)_n$—$CH_3$, when p is one or 2, n is zero to 3 and X is oxygen or sulfur. Alternatively, the starting compound, C-3, may be dissolved in methanol and treated with an aldehyde and sodium cyanoborohydride, when the aldehyde is HOC—($C_1$-$C_7$)alkyl, HOC—($C_3$-$C_8$)cycloalkyl, HOC—$(CH_2)_p$—$R_5$, or HOC—$CH_2$—X—$(CH_2)_n$—$CH_3$, when p is one or 2, n is zero to 3 and X is oxygen or sulfur.

In addition, an amide of the formula, C-4, when $R_d$ is ($C_1$-$C_7$) alkyl, ($C_3$-$C_8$)cycloalkyl, $(CH_2)_p$—$R_5$, or —$CH_2$—X—$(CH_2)_n$—$CH_3$, when p is one or 2, n is zero to 3 and X is oxygen or sulfur, may be reduce by a hydride reducing agent such as lithium aluminum hydride in ether or tetrahydrofuran, diborane in tetrahydrofuran or $QBH_4$ (where Q represents tetrabutylammonium ion) in a mixture of dichloromethane and dichloroethane, to give a compound of Formula I. Compounds of this invention wherein $R_1Y$ is —S($C_1$-$C_3$)alkyl can be prepared from a compound corresponding to a C-4 compound wherein $OR_1$ is replaced by a hydroxy group by converting the hydroxy group to an amine which is subsequently converted to bromine via a Sandmeyer reaction. The bromine substituted intermediate is lithiated using n-butyllithium in THF or ether and quenched with ($C_1$-$C_3$)alkyl-SS-alkyl($C_1$-$C_3$) to the alkylthio substituted compounds.

Starting materials for the compounds, C-1 to C-4, may be obtained by the methods described below or by methods known in the art. The known or commercially available ketone, C-5, when $R_1$ is alkyl, alkenyl, cycloalkyl, or benzyl, reacts with hydroxylamine in the presence of base to give the intermediate oxime which is reduced by catalytic hydrogenation to a compound of formula, C-6. To obtain the secondary amine a compound of the formula, C-6, is acylated with a carboxylic acid chloride in the presence of triethylamine and subsequently reduced by a hydride reducing agent such as lithium aluminum hydride in ether or tetrahydrofuran, diborane in tetrahydrofuran or $QBH_4$ (where Q represents tetrabutylammonium ion) in a mixture of dichloromethane and dichloroethane. Alternatively, the ketone, C-5, can be converted directly to the secondary amine, C-6, by reacting the ketone with a primary amine of the formula $R_e$—$NH_2$, when $R_e$ is alkyl, cycloalkyl, heterocyclic alkyl, ethylalkoxy or ethylthiaalkyl, with sodium cyanoborohydride in methanol acidified to about pH 5 with the addition of a few drops of concentrated acetic acid.

The preparation of the compounds of this invention with an alkyl group at the one position of the aliphatic ring are obtained by alkylating a compound of formula, C-7, either via the enamine or by direct alkylation of the ketone, C-7, under basic conditions, to give a compound of formula, C-5, converting compound, C-5, into the secondary amine using methods already described, separation of the cis- and trans- isomers formed, and finally converting the secondary amine into the tertiary amine using methods already described.

A pure enantiomer of compound, C-3, may be prepared by converting the cis-secondary amine, C-3, into the (−)-O-methylmandelic acid amide, C-8, followed by chromatographic separation of the two diastereomers and cleavage by subsequent reaction with potassium tertbutoxide in tetrahydrofuran with traces of water and methyl lithium. The secondary amine can be converted into the tertiary amine using methods already described.

In clinical practice the compounds of the present invention will normally be administered orally, rectally, or by injection, in the form of pharmaceutical preparations comprising the active ingredient either as a free base or as a pharmaceutically acceptable non-toxic, acid addition salt, such as the hydrochloride, lactate, acetate, sulfamate salt, in association with a pharmaceutically acceptable carrier. The use and administration to a patient to be treated in the clinic would be readily apparent to a person of ordinary skill in the art.

In therapeutic treatment the suitable daily doses of the compounds of the invention are 1–2000 mg for oral application, preferentially 50–500 mg, and 0.1–100 mg for parenteral application, preferentially 0.5–50 mg.

The compounds of this invention where —$OR_1$ is in the 8 position in the aromatic ring are very selective 5-$HT_{1A}$ receptor agonists having little or no dopaminergic activity. The IC50 ratio of dopamine $D_2$ to $5HT_{1A}$ in vitro binding data shown in Table 1 for one compound of this invention, 8-methoxy-2-(N,N-dicyclopropylmethyl)tetralin, demonstrates the selectivity for the 5-$HT_{1A}$ receptor. These compounds are particularly effective anxiolytic and antidepressant agents. Other uses for these compounds include panic attacks, obsessive-compulsive disturbances, and senile dementia particularly the emotional disturbances seen in dementia disorders. In addition, central 5-HT receptor activation are believed to be involved in mediating sexual behavior. These compounds would be useful to stimulate sexual activity and to alleviate impotence.

The compounds of this invention where —$OR_1$ is in the 5-, 6-, or 7-position show selective affinity for $D_2$ receptors. These compounds are particularly effective in treating psychoses, mano-depressive illness and parkinsonism.

The compounds of this invention also have been shown to have high oral potency and a long duration of action. Both these features are beneficial to effective clinical treatment.

The utility of the compounds of this invention to treat central nervous system disorders is shown in behavioral and biochemical activity in reserpine-pretreated rats. Antagonism of the reserpine-induced "neuroleptic syndrome" in the rat (gross behavior)

Depletion of the monoamine stores with reserpine brings about a "neuroleptic syndrome" characterized by hypomotility, catalepsy, muscle rigidity, hunch-backed posture as well as a number of other central and peripheral signs of monoamine depletion. The whole or parts of this syndrome can be reversed by the administration of drugs that stimulate dopamine or 5-HT receptors directly or indirectly.

Stimulation of the dopamine receptors, with apomorphine for example, gives rise to both locomotion and stereotyped behavior such as sniffing, gnawing and jumping. On the other hand, stimulation of the 5-HT receptors, with 5-hydroxytryptophane (5-HTP) combined with MAO-inhibitors for example, gives rise to a very different behavior. The animals lie flat on the cage floor exhibiting forward movements with extended forepaws padding, "piano-playing," and abducted hindlegs, occasionally with some tremor in the forebody and with Straub tail, stiff tail erection.

In-vivo determination of rat brain tyrosine and tryptophan hydroxylation after reserpine pretreatment (biochemically monitored dopamine and 5-HT receptor activity)

The compounds under evaluation were tested biochemically for central dopamine and 5-HT receptor (pre- and/or postsynaptic) stimulating activity. The concept of this biochemical screening method is that a dopamine or 5-HT-receptor agonist will stimulate the receptor and through regulatory feedback systems effect a decline in tyrosine or tryptophan hydroxylating activity, respectively, and a subsequent reduction in the synthesis rate for dopamine and 5-HT in the presynaptic neuron. Dopamine and 5-HTP formation, as determined after in-vivo inhibition of the aromatic L-amino acid decarboxylase with NSD 1015 (3-hydroxybenzylhydrazine hydrochloride) are taken as indirect measures of dopamine and 5-HT-synthesis rates, respectively.

Analogous conditions probably exist also for central NA-neurons. Effects on the dopamine formation in the NA-predominated hemispheral parts (mainly cortex) may thus be considered to reflect NA-receptor-mediated changes.

EXPERIMENTAL PROCEDURES

Rats (150–300 g) pretreated with reserpine (5 mg/kg, 18 hours before) were given the test compounds. Gross behavioral observations (changes in motility, hindleg abduction, etc.) were made. Subsequent administration of NSD 1015, decapitation, brain dissection (corpora striata, the limbic forebrain and the remaining hemispheral portions (mainly cortex) or rat brain), homogenization, centrifugation, ion-exchange chromatography and spectrofluorimetric measurements (all as described in detail by Wikstrom, et al., J. Med. Chem., 21, 864–867, 1978 and reference cited therein), or by HPLC/EC, gave the actual dopamine and 5-HTP levels. Several doses (n-4–6) were tested for each compound and brain area. The dose of a compound giving 50% of the maximal reduction of the %-HTP level in the rat brain part was then estimated. These ED50 values are presented in Table I.

All the compounds in Table 1 were both behaviorally and biochemically active, producing the above mentioned effects indicating either central dopamine or 5-HT receptor stimulation. The absence of significant decreases in the dopamine levels in the hemispheral brain parts suggests that none of the compounds possess central NA receptor stimulating effects at the dosage under consideration.

Certain compounds of the present invention also demonstrate blood pressure lowering effects, e.g., the compounds of Examples 12, 13, and 17 when measured in spontaneously hypertensive rats as described by Grodin, et al., J. Pharm. Pharmacol. 37, 263–265 (1984). Without further elaboration, it is believed that one skilled in the art can, using the preceding description, practice the present invention to its fullest extent.

The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLES

8-Methoxy-2-(N-cyclopropylmethylamino)tetralin

8-Methoxy-2-aminotetralin hydrochloride (0.5 g, 2.35 mmol) is dissolved in dichloromethane (50 ml), and triethylamine (3 ml) and cyclopropanecarboxylic acid chloride (0.95 ml) are added. The reaction is stopped after 2 hours by the addition of 10% sodium carbonate (50 ml). The organic layer is separated, washed with water (50 ml), dried over sodium carbonate, filtered and the solvent is evaporated yielding the amide as an oil (0.85 g). The amide is dissolved in dichloromethane (25 ml) and reduced with the addition of dichloroethane (25 ml) and QBH$_4$ (2.5 g) (where Q denotes the tetrabutylammonium ion) under reflux for 6 hours. The reaction is stopped by the addition of 10% sodium carbonate (100 ml) and dichloromethane (2×100 ml). The organic layer is separated, washed with water (50 ml) dried (sodium carbonate), filtered and the solvent evaporated yielding the amine (95% purity according to GC analysis) as an oil (0.47 g). This amine is converted to the hydrochloride salt with the aid of hydrochloric acid-saturated ethanol and evaporation. Recrystallization from ethanol/ether gives white crystals (0.38 g) melting at 214° C. GC/MS shows M+ as the base peak at m/e=231.10. Other prominent peaks appear at m/e=161.05 (m-cyclopropylmethylamine; 48.8%), m/e=160.05 (53.2%) and m/e=159.05 (37.3%).

EXAMPLE 2

8-Methoxy-2-(N,N-di-cyclopropylmethylamino)tetralin

8-Methoxy-2-(N-cyclopropylmethylamino)tetralin hydrochloride (0.36 g, 1.35 mmol) is dissolved in dichloromethane (50 ml), and triethylamine (1 ml) and cyclopropanecarboxylic acid chloride (0.35 ml) are added. The reaction is stopped after 2 hours by the addition of 10% sodium carbonate (50 ml). The organic layer is separated, washed with water (50 ml), dried (sodium carbonate), filtered and the solvent is evaporated leaving the amide as an oil (0.47 g), which is dissolved in dichloromethane (25 ml) and reduced with the addition of dichloroethane (25 ml) and QBH$_4$ (2.5 g) (where Q denotes the tetrabutylammonium ion) under reflux for 2 hours. The reaction is not complete at this time according to GC analysis, and further addition of QBH$_4$ (2.5 g) and dichloroethane (25 ml) is made. The reaction is stopped after one night's reflux by the addition of 10% sodium carbonate (100 ml) and dichloromethane (2×100 ml). The organic layer is separated, washed with water (50 ml), dried (sodium carbonate), filtered and the solvent is evaporated yielding the amine as an oil (0.40 g). The amine is chromatographed (silica gel, 40 g) eluting first with petroleum ether:ether (3:1) and then with ether. The fractions containing pure product are pooled and the solvent is evaporated. The residual amine is converted into the hydrochloride by the addition of hydrochloric acid-saturated ethanol and evaporation. Recrystallization from ethyl acetate/ether gives white crystals (114 mg) melting at 174°–176° C. GC/MS shows M+ at m/e=285.25 (54.8%), the base peak at m/e=136.10. Other prominent peaks appear at m/e=244.15 (m-cyclopropyl; 25.0%), m/e=161.05 (m-(di-cyclopropylmethylamine); 63.5%).

The remaining fractions are collected and the solvent is evaporated yielding 150 mg of an oil holding 70% of the intermediate amide. The oil is dissolved in dry ether (10 ml) and reduced with lithium aluminum hydride and converted into the hydrochloride salt as described above and recrystallization as above gives 126 mg of white crystals with the same characteristics as those obtained initially.

EXAMPLE 3 cis-5-Methoxy-1-methyl-2-(N-cyclopropylmethylamino)tetralin

To a solution of 5-methoxy-1-methyl-2-tetralone (2.0 g) in absolute ethanol (50 ml) are added acetic acid (1.9 g), cyclopropylmethylamine (2.0 g) and 4 Å molecular sieves. The mixture is heated in a closed flask at 80° C. for one hour. The molecular sieves are filtered off and the solution is hydrogenated (PtO$_2$) at atmospheric pressure. The catalyst is filtered off (Celite) and the volatiles are evaporated. Dilute hydrochloric acid (50 ml) is added to the solid residue. The resulting acidic solution is washed with ether, made basic 5% sodium hydroxide and extracted twice with ether. The ether extracts are combined, dried (sodium sulfate) and evaporated. The resulting crude base is eluted through an alumina column with ether-light petroleum (1:4).

EXAMPLE 4 cis-5-Methoxy-1-methyl-2-(N,N-dicyclopropylmethylamino)tetralin hydrochloride

Cyclopropanecarboxylic acid chloride (0.49 g) in dry ether (10 ml) is added to a solution of cis-5-methoxy-1-methyl-2-(N-cyclopropylmethylamino)tetralin (400 mg) and triethylamine (0.49 g) in dry ether (80 ml). After 30 minutes at room temperature the reaction mixture is filtered and the ether is evaporated. The resulting crude amide is passed through an alumina column eluted with ether. The purified amide dissolved in dry THF (20 ml) is added to a suspension of lithium aluminum hydride (1.0 g) in dry THF (30 ml) under N$_2$. After stirring under reflux for 3 hours, the reaction mixture is hydrolyzed, the precipitate is filtered off and the solvent is evaporated. The oily residue is chromatographed on an alumina column with ether-light petroleum (1:1). The hydrochloride is prepared and recrystallized from ethanol-ether to give the title compound.

EXAMPLE 5

(+) and (−)-cis-5-Methoxy-1-methyl-2-(N,N-dicyclopropylmethylamino)tetralin hydrochloride (−)-cis-5-Methoxy-1-methyl-2-(N,N-dicyclopropylmethylamino)tetralin hydrochloride R-(−)-O-Methylmandelic acid chloride (4.1 g), prepared from R-(−)-O-methylmandelic acid by treatment with thionylchloride at 20° C. for 10 hours, dissolved in dichloromethane (5 ml) is added at room temperature to a stirred mixture of (±)-cis-5-methoxy-1-methyl-2-(N-cyclopropylamino)tetralin (3.0 g), dichloromethane (25 ml), water (25 ml) and 5% aqueous sodium hydroxide (12 ml). After stirring for 1.5 hour the phases are separated and the organic phase is washed once with water then dried (magnesium sulfate), filtered and evaporated. Ether (15 ml) is added to the residue and one of the diastereomeric amides precipitated (1.2 g). The precipitate is collected by filtration and then recrystallized from acetone to give 1.0 g of one of the diastereomers. The filtrates from the treatment with ether and acetone are combined and evaporated. This oily residue is chromatographed on a silica gel column with ether/light petroleum (50:50). The fractions containing one of the diastereomers, which is eluted first are combined and the solvent is evaporated to give 0.6 g of one of the diastereomeric amides. This diastereomer shows to be the same diastereomeric amide (TLC) as is isolated by precipitation from ether (see above). The diastereomeric amide (1.6 g) is dissolved in dry tetrahydrofuran (40 ml) and kept at −8° C. under nitrogen. To this solution is added potassium-tert-butoxide (21.1 g) and water (0.60 ml) with the addition divided in seven portions over 12 days. Thirteen days after the first addition of reagents ice, water and ether is added to the reaction mixture until 2 layers form. The phases are separated and the organic layer is washed with 1M hydrochloric acid, saturated aqueous sodium bicarbonate, dried (magnesium sulfate), filtered and evaporated. The residue, dissolved in ether-light petroleum (50:50), is passed through a silica gel column and eluted first with ether-light petroleum (50:50) and then with ether, yielding a solid (0.55 g) after evaporation. To this solid (0.56 g), dissolved in dry tetrahydrofuran (40 ml) at 8° C. and under nitrogen, methyl lithium (0.0054 mol) is added under stirring. The mixture is stirred for 10 minutes, then extracted with saturated aqueous NH$_4$Cl. The phases are separated and the organic layer is extracted with 5M hydrochloric acid. The combined aqueous layers are made basic with 5M sodium hydroxide and extracted with ether. The organic layer is dried (sodium sulfate) and filtered. Hydrochloric acid-saturated ether is added giving a precipitate which is recrystallized giving (−)-cis-5-methoxy-1-methyl-2-(N-cyclopropylmethylamino)tetralin hydrochloride.

Cyclopropanecarboxylic acid chloride (0.28 g) in dry ether (5 ml) is slowly added at 5° C. to a solution of (−)-cis-5-methoxy-1-methyl-2-(N-cyclopropylmethylamino)tetralin (0.35 g), triethylamine (0.31 g) and dry ether (45 ml). The mixture is stirred at room temperature for one hour, the triethylammoniumchloride formed is filtered off and the solvent evaporated. The residue (0.40 g) dissolved in dry tetrahydrofuran (10 ml) is added to a suspension of lithium aluminum hydride (0.80 g) in dry tetrahydrofuran (40 ml) under nitrogen. After stirring under reflux for 5 hours, the mixture is hydrolyzed, the precipitate is filtered off, and the solvent is evaporated. The residue is passed through an alumina column with ether/light petroleum (20:80), and the amine is precipitated as the hydrochloride and recrystallized from ethanol-ether to give (−)-cis-5-methoxy-1-methyl-2-(N,N-dicyclopropylmethylamino)tetralin hydrochloride.

EXAMPLE 6

(±)-cis-7-methoxy-1-methyl-2-(N-cyclopropylmethylamino)tetralin

To a solution of 7-methoxy-1-methyl-2-tetralone (2.0 g) in absolute ethanol (50 ml) are added acetic acid (1.85 g, 31.5 mmol), cyclopropylmethylamine (1.85 g) and 4 Å molecular sieves. The mixture is refluxed for 3.5 hours. The molecular sieves are filtered off and the solution is hydrogenated with 0.3 g PtO$_2$ in a Parr apparatus. The catalyst is filtered off (Celite) and the volatiles are evaporated. The resulting crude base is eluted through an silica gel column with methanol, affording an oil of 80% isomeric purity (GC). The hydrochloride is prepared and recrystallized 2 times from methanol-ether.

EXAMPLE 7

(±)-cis-7-methoxy-1-methyl-2-(N,N-dicyclopropylmethylamino)tetralin

Sodium borohydride (0.41 g, 10.1 mmol) is added portionwise to a stirred solution of cyclopropanecarboxylic acid chloride (2.4 g) in dry benzene (20 ml) under N$_2$, keeping the temperature below 20° C. After 2 hours, (±)-cis-7-methoxy-1-methyl-2-(cyclopropylmethylamino)tetralin (0.5 g) is added and the mixture is refluxed for 4 hours and then treated with 10% sodium bicarbonate solution. The benzene layer is dried (sodium sulfate) and the solvent is evaporated. The hydrochloride salt is prepared and recrystallized from methanol-ether.

EXAMPLE 8

Preparation of Soft Gelatine Capsules 500 g of active substance are mixed with 500 g of corn oil, whereupon the mixture is filled in soft gelatine capsules, each capsule containing 100 mg of the mixture.

EXAMPLE 9

Preparation of Tablets 0.5 kg of active substance are mixed with 0.2 kg of silicic acid of the trademark Aerosil. Potato starch (0.45 kg) and lactose (0.5 kg) are mixed therewith and the mixture is moistened with a starch paste prepared from 50 g of potato starch and distilled water, whereupon the mixture is granulated through a sieve. The granulate is dried and sieved, whereupon 20 g of magnesium stearate are mixed into it. Finally the mixture is pressed into tablets each weighing 172 mg.

EXAMPLE 10

Preparation of a Syrup 100 g of active substance are dissolved in 300 g of 95% ethanol, whereupon 300 g of glycerol, aroma and coloring agents (q.s.) and 1000 ml of water are mixed therein. A syrup is obtained.

EXAMPLE 11

Preparation of an injection solution

Active substance (1 g), sodium chloride (0.8 g) and ascorbic acid (0.1 g) are dissolved in sufficient amount of distilled water to give 100 ml of solution. This solution, which contains 10 mg of active substance per ml, is used in filling ampoules, which are sterilized by heating at 120° C. for 20 minutes.

EXAMPLE 12

(+)-R-8-Methoxy-2-(di-cyclopropyl-methylamino)tetralin

The resolution is performed on 8-methoxy-2-(benzylamino)tetralin with the aid of (−)-di-p-toluoyltartaric acid according to Karlsson, et al., Acta Chem. Scand., B 42, 231–236 (1988). The enantiomers of 8-methoxy-2-(benzylamino)tetralin are debenzylated, yielding the corresponding enantiomers of 8-methoxy-2-aminotetralin, i.e., R-(+)- and S-(−)-8-methoxy-2-aminotetralin.

The primary amine (+)-R-8-methoxy-2-aminotetralin (3.29 g) is acylated with cyclopropanecarboxylic acid chloride (1.8 ml) and the amide produced (3.63 g) is reduced with QBH$_4$ as described in above, yielding the secondary amine, which is acylated again in the same way with cyclopropanecarboxylic acid chloride (3.2 ml). The amide produced (3.57 g) is dissolved in dry THF (25 ml) and reduced with LiAlH$_4$ at room temperature. Usual workup yields the raw tertiary amine product (2.9 g), which is chromatographed (SiO$_2$; eluting with CH$_2$Cl$_2$:MeOH (19:1)), yielding pure product (2.1 g) as an oil, which is converted to its hydrochloride with HCl-saturated EtOH and evaporation of the solvent and excess acid. No crystals are obtained in an attempt to crystallize the product. The optical rotation is: $\alpha_D^{22} = +68°$ (c 1.0, MeOH).

GC/MS shows M+ at m/e=285 (61%) and the base peak at m/e=136. Other prominent peaks appear at m/e=244 (30%), 161 (72%) and m/e=160 (42%).

EXAMPLE 13

(−)-R-8-Methoxy-2-(di-cyclopropylmethylamino)tetralin

The primary amine (−)-R-8-methoxy-2-aminotetralin (5.0 g) is converted into the secondary amine (−)-R-8-methoxy-2-(cyclopropylmethylamino)tetralin, which is further converted into the tertiary amine (−)-R-8-methoxy-2-(di-cyclopropylmethylamino)tetralin (2.42 g) as described for the corresponding (+)-enantiomer in Example 3 above. The optical rotation is: $\alpha_D^{22} = -66°$ (c 1.0, MeOH).

GC/MS shows M+ at m/e=285 (83%) and the base peak at m/e=136. Other prominent peaks appear at m/e=244 (33%), 161 (67%) and m/e=160 (40%).

EXAMPLE 14

8-Methoxy-2-(N-cyclopropylmethyl-N-ethylamino)tetralin

8-Methoxy-2-(cyclopropylmethylamino)tetralin (200 mg) is dissolved in CH$_2$Cl$_2$ (25 ml) and the solution is basified by the addition of Et$_3$N (3 ml). Acetylchloride (150 μl) is added and the reaction mixture is left stirring for 3 hours. 10% Na$_2$CO$_3$ is added and the raw amide product is extracted to the organic layer, which is dried and filtered. The organic solvent is removed by evaporation yielding 210 mg of the amide as an oil, which is dissolved in dry ether (10 ml). This solution is added to a suspension of LiAlH$_4$ (0.3 g) in dry ether (10 ml) and the temperature is kept at about 0° C. with an ice bath. Usual workup (0.3 ml water, 0.3 ml 15% NaOH, 0.9 ml water, filtration and ether extraction) gives 188 mg of an oil, which is chromatographed (200 g SiO$_2$; eluting with CH$_2$Cl$_2$: MeOH (19:1)), yielding the product as an oil (66 mg).

GC/MS shows M+ at m/e=259 (70%) and the base peak at m/e=161. Other prominent peaks appear at m/e=244 (33%) and m/e=160 (30%).

EXAMPLE 15

8-Methoxy-2-(N-cyclopropylmethyl-N-n-propylamino)-tetralin

8-Methoxy-2-(n-propylamino)tetralin (350 mg) is dissolved in CH$_2$Cl$_2$ (20 ml) and Et$_3$N (1 ml) and cyclopropanecarboxylic acid chloride (0.5 ml) are added. Workup gives the amide (0.6 g) as an oil. The amide is dissolved in dry ether and reduced with LiAlH$_4$ (0.9 g). The reaction is quenched after 2 hours in the usual way (0.9 ml H$_2$O, 0.9 ml 15% NaOH and 2.7 ml H$_2$O) and workup yields an oil, which is chromatographed on SiO$_2$ (70 g), eluting with petroleumether: ether (1:1). The fractions containing pureproduct are pooled and the solvent is evaporated yielding an oil (210 mg) which is converted to the hydrochloride with HCl-saturated EtOH and evaporation of the solvent. Crystals (170 mg) are obtained from aceton: ether, and they melt at 143°–145° C.

GC/MS shows M+ at m/e=273.15 (24.5%) and the base peak at m/e=161.05. Other prominent peaks appear at m/e=245.05 (14.3%), m/e=244.05 (87.1%) and m/e=162.05 (18.8%).

EXAMPLE 16

7-Methoxy-2-(N-cyclopropylmethyl-N-n-propylamino)-tetralin

7-Methoxy-2-(n-propylamino)tetralin (500 mg) is dissolved in CH$_2$Cl$_2$ (25 ml) and the solution is basified by the addition of Et$_3$N (3 ml). Cyclopropanecarboxylic acid chloride (195 μl) is added and the reaction mixture is left stirring for 4 hours. 10% Na$_2$CO$_3$ is added and the raw amide product is extracted to the organic layer, which is dried and filtered. The organic solvent is removed by evaporation yielding 500 mg of the amide (GC/MS shows M+ at m/e=287.15 (0.3%) and the base peak at m/e=160.10) as an oil, which is dissolved in 1,2-dichloroethane (50 ml). To this solution is added QBH$_4$ (where Q means tetrabutylammonium) (5.0 g) dissolved in CH$_2$Cl$_2$ (50 ml). The reaction mixture is refluxed for 36 hours and is then chilled to room temperature and extracted with water several times. The solvents of the organic phase are evaporated and to the residue is added ether. The ether phase is washed with water several times, separated, dried ($Na_2SO_4$), filtered and the solvent is evaporated to give 453 mg of an oil, which is chromatographed (200 g $SiO_2$; eluting with petroleumether:ether (9:1), yielding the product as an oil. This oil is converted to the hydrochloride with HCl-saturated EtOH and evaporation to yield an oil (436 mg).

GC/MS shows M+ at m/e=273.15 (27.1%) and the base peak at m/e=244.15. Other prominent peaks appear at m/e=161.10 (76.9%).

EXAMPLE 17

8-Methoxy-2-(N-cyclopropylmethyl-N-(2-thiophenethyl)-amino)tetralin

8-Methoxy-2-aminotetralin (800 mg) is stirred in a two phase system (10% $Na_2CO_3$ and $CH_2Cl_2$) and 2-thiopheneacetic acid chloride (1 g) is added. The reaction mixture is stirred for 2 hours and then the organic phase is separated, dried ($Na_2SO_4$) and filtered. The solvent is evaporated to give the amide as an oil (1.5 g). The amide is reduced with $QBH_4$ (1 g) in a refluxing (8 hours) mixture of $CH_2Cl_2$ (50 ml) and 1,2-dichloroethane (50 ml). The reaction mixture is chilled to room temperature and the organic layer is washed several times with water. The organic layer is separated and the solvents are evaporated, yielding an oil, which is treated with EtOAc and water. This mixture is acidified with HCl (10%) and stirred for 30 minutes and then the mixture is basified. The organic layer is separated, dried ($Na_2SO_4$) and filtered. The solvent is evaporated to give the amine as an oil (900 mg). This oil (400 mg) is dissolved in $CH_2Cl_2$ (25 ml) and $Et_3N$ (1 ml) and cyclopropanecarboxylic acid chloride (1.0 ml) is added and the reaction mixture is left stirring for one hour. 10% $Na_2CO_3$ is added and the raw amide produce is extracted to the organic layer, which is dried and filtered. The organic solvent is removed by evaporation yielding 600 mg of the amide as an oil, which is chromatographed ($SiO_2$ and eluting with petroleumether: ether (2:1)), yielding 270 mg of the pure amide. This amide (270 mg) is dissolved in 1,2-dichloroethane (20 ml). To this solution is added $QBH_4$ (where Q means tetraethylammonium) (1.0 g) dissolved in $CH_2Cl_2$ (20 ml). The reaction mixture is refluxed for 12 hours and is then chilled to room temperature and extracted with water several times. The solvents of the organic phase are evaporated and to the residue is added EtOAc (20 ml). The organic phase is washed with water several times, separated, dried ($Na_2SO_4$), filtered and the solvent is evaporated to give 220 mg of an oil, which is chromatographed (20 g $SiO_2$; eluting with petroleumether:ether (1:1)), yielding the product as an oil (160 mg). This oil is converted to the hydrochloride with HCl-saturated EtOH and evaporation of the solvent to yield an oil (170 mg).

GC/MS shows M+ at m/e=340.20 (0.1%), m/e=341.10 (0.1%), and the base peak at m/e=161.10. Other prominent peaks appear at m/e=245.20 (11.6%) and m/e=244.20 (63.8%).

EXAMPLE 18

5-Methoxy-2-(cyclopropylmethylamino)tetralin

5-Methoxy-2-aminotetralin (972 mg) is dissolved in $CH_2Cl_2$ (20 ml) and $Et_3N$ (3 ml) is added together with cyclopropanecarboxylic acid chloride (550 μl). The reaction mixture is left stirring for one hour. 10% $Na_2C\eta_3$ is added and the raw amide product is extracted to the organic layer, which is dried and filtered. The organic solvent is removed by evaporation yielding 1.16 g of the amide as an oil, which is chromatographed ($SiO_2$ and eluting with $CH_2Cl_2$:MeOH (45:1)), yielding 0.98 mg of the pure amide (GC/MS shows M+ at m/e=245 (61%) and the base peak at m/e=160. Other prominent peaks appear at m/e=159 (26%), m/e=145 (19%) and m/e=129 (18%)). This amide (0.98 g) is dissolved in 1,2-dichloroethane (30 ml). To this solution is added $QBH_4$ (where Q means tetrabutylammonium) (2.0 g) dissolved in $CH_2Cl_2$ (30 ml). The reaction mixture is refluxed for 24 hours and then chilled to room temperature and extracted with water several times. The solvents of the organic phase are evaporated and to the residue is added EtOAc (20 ml). The organic phase is washed with water several times, separated, dried ($Na_2SO_4$), filtered and the solvent is evaporated to give 800 mg of an oil, which is chromatographed (200 g $SiO_2$; eluting with $CH_2Cl_2$:MeOH (19:1)), yielding the product as an oil (800 mg).

GC/MS shows M+ as the base peak at m/e=231. Other prominent peaks appear at m/e=161 (62%), m/e=160 (83%), m/e=159 (64%), and m/e=104 (92%).

EXAMPLE 19

5-Methoxy-2-(dicyclopropylmethylamino)tetralin 5-methoxy-2(dicyclopropylmethylamino)tetralin (410 mg) is dissolved in $CH_2Cl_2$ (20 ml) and $Et_3N$ (3 ml) is added together with cyclopropanecarboxylic acid chloride (400 μl). The reaction mixture is left stirring for 48 hours. 10% $Na_2CO_3$ is added and the raw amide product is extracted to the organic layer, which is dried and filtered. The organic solvent is removed by evaporation yielding 520 of the amide as an oil. This raw amide (520 mg) is dissolved in dry THF (15 ml) and this solution is added dropwise to a suspension of $LiAlH_2$ (0.5 g) in dry THF (10 ml). The reaction mixture is stirred at room temperature for one hour and usual workup gives 385 mg of the desired product as an oil (GC/MS shows M+ at m/e=285.20 (40%), base peak at m/e=136.05. Other prominent peaks appear at m/e=244.10 (30.1%), m/e=161.05 (37.9%, m/e=), m/e=160.15 (30.2%), and m/e=159.05 (13.2%). The product is converted to a crystalline hydrochloride and crystals, melting at 150–153° C., are obtained from EtOH: ether.

EXAMPLE 20

5-Methoxy-2(N-cyclopropylmethyl-N-n-propylamino)-tetralin

5-Methoxy-2-(cyclopropylmethylamino)tetralin (390 mg) is dissolved in $CH_2Cl_2$ (20 ml) and $Et_3N$ (3 ml) is added together with propionic acid chloride (300 μl). The reaction mixture is left stirring for 5 hours. 10% $Na_2CO_3$ is added and the raw amide product is extracted to the organic layer, which is dried and filtered. The organic solvent is removed by evaporation yielding 469 mg of the amide as an oil. This raw amide (469 mg) is dissolved in dry ether (15 ml) and this solution is added dropwise to a suspension of $LiAlH_4$ (0.45 g) in dry ether (10 ml). The reaction mixture is stirred at room temperature for one hour and usual workup gives 324 mg of the desired product as an oil, which is chromatographed ($SiO_2$ and eluting with $CH_2Cl_2$:MeOH (19:1), yielding 201 mg of the desired product as an oil.

GC/MS shows M+ at m/e=273.20 (25.0%), base peak at m/e=244.25. Other prominent peaks appear at m/e=245.25 (18.6%), m/e=244.05 (87.1%) and m/e=161.15 (75.3%).

EXAMPLE 21

(+)-cis-1S,2R-5-Methoxy-1-methyl-2-(N-cyclopropyl-methyl-N-n-propylamino)tetralin (+)-cis-1S, 2R-5-Methoxy-1-methyl-2-(n-propylamino)tetralin (500 mg) is dissolved in $CH_2Cl_2$ (20 ml) and $Et_3N$ (3 ml) is added together with cyclopropanecarboxylic acid chloride (300 µl). The reaction mixture is left stirring for one hour. 10% $Na_2CO_3$ is added and the raw amide product is extracted to the organic layer, which is dried and filtered. The organic solvent is removed by evaporation yielding 550 mg of the amide as an oil. This raw amide (550 mg) is dissolved in dry ether (15 ml) and this solution is added dropwise to a suspension of $LiAlH_4$ (0.60 g) in dry ether (10 ml). The reaction mixture is stirred at room temperature overnight and usual workup gives 483 mg of the desired product as an oil, which is chromatographed (100 g $SiO_2$ and eluting with hexane:ether (3:1)), yielding the desired product as an oil (280 mg). This oil is converted to the hydrochloride salt, but no crystals are achieved.

GC/MS shows M+ at m/e=287.15 (25.8%) and the base peak at m/e=258.15. Other prominent peaks appear at m/e=259.15 (19.5%), m/e=176.10 (12.4%), m/e=175.10 (88.6%) and m/e=174.20 (17.4%), The optical rotation is measured and found to be: $\alpha_D^{22}=+38°$ (c 1.0, MeOH).

EXAMPLE 22

(+)-cis-1S,2R-5-Methoxy-1-methyl-2-(cyclopropylme-thylamino)tetralin (+)-cis-1S,2R-5-Methoxy-1-methyl-2-aminotetralin (970 mg) is dissolved in $CH_2Cl_2$ (20 ml) and $Et_3N$ (3 ml) is added together with cyclopropanecarboxylic acid chloride (500 µl). The reaction mixture is left stirring for one hour. 10% $Na_2CO_3$ is added and the raw amide product is extracted to the organic layer, which is dried and filtered. The organic solvent is removed by evaporation yielding 1.0 g of the amide as an oil. This raw amide (1.0 g) is dissolved in 1,2-dichloroethane (60 ml). To this solution is added $QBH_4$ (where Q means tetrabutylammonium) (1.4 g) dissolved in $CH_2Cl_2$ (60 ml). The reaction mixture is refluxed for 48 hours and is then chilled to room temperature and extracted with water several times. The solvents of the organic phase are evaporated and to the residue is added trichlorethylene. The organic phase is washed with water several times, separated, dried ($Na_2SO_4$), filtered and the solvent is evaporated to give 840 mg of an oil, which is converted to the hydrochloride with HCl-saturated EtOH and evaporation to yield crystals (750 mg) melting at 212° C.

GC/MS shows M+ at m/e=245.15 (53.5%) and the base peak at m/e=148.10. Other prominent peaks appear at m/e=190.20 (15.6%), m/e=175.10 (18.2%), m/e=174.10 (44.8%), m/e=173.20 (10.3%) and m/e=159.10 (45.9%). The optical rotation is measured and found to be: $\alpha_D^{22}=+49.1°$ (c 1.0, MeOH).

EXAMPLE 23

(+)-cis-1S,2R-5-Methoxy-1-methyl-2-(N-cyclopropyl-methyl-N-(3-methoxyphenylethyl)amino)tetralin (+)-cis-1S,2R-5-Methoxy-1-methyl-2-(cyclopropyl-methylamino)tetralin (50 mg) was dissolved in $CH_2Cl_2$ (5 ml) and 10% NaOH (5 ml) was added together with 3-methoxyphenylacetic acid chloride (50 µl). The reaction mixture was left stirring for one hour. The raw amide product was extracted to the organic layer, which was dried and filtered. The organic solvent was removed by evaporation yielding 60 mg of the amide as an oil. This raw amide (60 mg) was dissolved in 1,2-dichloroethane (10 ml). To this solution was added $QBH_4$ (where Q means tetraethylammonium) (200 mg) dissolved in $CH_2Cl_2$ (30 ml). The reaction mixture was refluxed overnight and was then chilled to room temperature and extracted with water several times, separated, dried ($Na_2SO_4$), filtered and the solvent was evaporated to give 60 mg of the desired product as an oil, which was chromatographed (15 g $SiO_2$ and eluting with hexane:ether (3:1)), yielding the desired product as an oil (20 mg). This oil was converted to the hydrochloride salt, but no crystals were achieved.

GC/MS shows M+ at m/e=379.20 (0.1%) and the base peak at m/e=258.20. Other prominent peaks appeared at m/e=259.20 (19.0%), m/e−176.10 (8.6%) and m/e=175.10 (65.3%). The optical rotation was measured and was found to be $\alpha_D^{22}=+35°$ (c 1.0, MeOH).

EXAMPLE 24

(+)-R-8-Methoxy-2-(N-cyclopropylmethyl-N-(3-methoxyphenylethyl)amino)-tetralin (+)-R-8-Methoxy-1-methyl-2-(cyclopropylme-thylamino)tetralin (250 mg) was dissolved in $CH_2Cl_2$ (25 ml) and 10% NaOH (25 ml) was added together with a 3-methoxyphenylacetic acid chloride (0.4 g). The reaction mixture was left stirring for 2 days. The raw amide product was extracted to the organic layer, which was dried and filtered. The organic solvent was removed by evaporation yielding 400 mg of the amide as an oil. This raw amide was chromatographed ($SiO_2$ and eluting with petroleumether:ether (3:1)). The fractions containing pure product were pooled and the solvent was evaporated yielding an oil (250 mg). The amide oil (250 mg) was dissolved in dry ether (10 ml). To this solution was added $LiAlH_4$ (100 mg). Usual workup gave the desired product as an oil (100 mg).

GC/MS showed M-1 at m/e−364.15 (0.1%) and the base peak at m/e=161.00. Other prominent peaks appeared at m/e−245.05 (16.2%) and m/e=244.05 (87.2%).

EXAMPLE 25

7-Methylthio-2-(N-cyclopropylmethyl(-N-n-propylamino)-tetralin

7-Bromo-2-(di-n-propylamin)tetralin HCl (600 mg) was converted to the base with 10% $Na_2CO_3$ and extraction with $CH_2Cl_2$. The organic layer was dried and filtered and the solvent was evaporated under reduced pressure. The residual oil was dissolved in dry THF (40 ml) and poured into a flask equipped with $N_2(g)$ inlet, a drug funnel, a thermometer and septum for syringe injections of reagents and sample collection. This flask was chilled to −78° C. and n-BuLi in hexane (1.4M, 3 ml) was injected through the septum. The reaction mixture was stirred for 0.5 hour for the halogen-lithium exchange to take place. This was checked with a small sample quenched in water and GC analysis. Dimethylsulfide (0.5 ml) was added dropwise from the funnel during 30 minutes at −78° C. The $CO_2(s)$-bath was removed and the temperature was allowed to reach room temperature before the reaction was quenched with water. Extractive workup yielded in oil (700 mg), which contained 2-(di-n-propylamino)tetralin and the desired product in an approximative ration of 45:55. This raw oil was chromatographed and the fractions containing pure product were pooled and the solvent was evaporated yielding 110 mg of the product as an oil, which was used in the next step without further purification. The oil (95 mg) was dissolved in $CH_2Cl_2$ (10 ml) and excess $Br_2$ (35 μl) was added. The organic phase was extracted with 10% $Na_2CO_3$ and separated. Excess $Br_2$ was removed with the addition of anisole (1 ml). The product in the organic phase was then extracted to 10% HCl and the acidic organic phase (containing the brominated anisoles) was discarded. The acidic water was basified (10% $Na_2CO_3$) and extracted with ether, dried ($Na_2CO_3$), filtered and the solvent was evaporated, yielding 40 mg of an oil.

GC/MS showed $M^+$ at m/e=235 (60%) and the base peak at m/e=129. Other prominent peaks appeared at m/e−206 (52%), m/e−192 (20%), m/e−177 (45%), m/e−176 (30%), m/e=175 (15%), m/e=151 (25%), m/e=150 (35%) and m/e=130 (50%).

The secondary amine produced (40 mg, 0.17 mmol) was dissolved in $CH_2Cl_2$ (5 ml) N-acylated with cyclopropanecarboxylic acid chloride (23 μl) in the presence of $Et_3N$ (50 μl). After 30 minutes the reaction mixture was washed with 10% $Na_2CO_3$ and the organic phase was separated, dried ($Na_2CO_3$), filtered and the solvent was evaporated, yielding 55 mg of an oil.

GC/MS showed $M^+$ at m/e=303 (1%) and the base peak at m/e−176. Other prominent peaks appeared at m/e=175 (15%), m/e=129 (45%) and 128 (25%).

The amide (55 mg) was dissolved in dry ether (10 ml) and reduced by the addition of $LiAlH_2$ (75 mg). Usual workup gave the raw product as an oil (29 mg), which was chromatographed ($SiO_2$ and eluting with petroleumether:ether (3:1)). The fraction containing the desired, pure 7-methylthio-2-N-cyclopropylmethyl-N-n-propylamin)tetralin were pooled and the solvent was evaporated, yielding 14 mg of an oil.

GC/MS showed $M^+$ at m/e=289 (35%) and the base peak at m/e=260. Other prominent peaks appeared at m/e=261 (20%), m/e=324 (10%), m/e=177 (25%), m/e=176 (10%), m/e=151 (10%), m/e=130 (40%), m/e=129 (45%), m/e=124 (20%) and m/e=84 (15%).

EXAMPLE 26

(+)-R-8-Methoxy-2-(cyclopropylmethylamino)tetralin (+)-R-8-Methoxy-2-(cyclopropylmethylamino)tetralin (500 mg) was dissolved in $CH_2Cl_2$ (25 ml) and 10% $Na_2CO_3$ (25 ml) was added together with acetyl chloride (0.4 g). The reaction mixture was left stirring for 2 hours. The raw amide product was extracted to the organic layer, which was dried and filtered. The organic solvent was removed by evaporation yielding the amide as an oil. This raw amide was chromatographed $SiO_2$ and eluting with petroleumether:ether (3.1)). The fractions containing pure product were pooled and the solvent was evaporated yielding an oil (324 mg). The amide oil (324 mg) was dissolved in dry ether (10 ml). To this solution was added $LiAlH_2$ (300 ml). Usual workup gave the desired product as an oil (290 mg), which was chromatographed ($SiO_2$ and eluting with $CH_2Cl_2$:MeOH (19.1)). The fractions containing pure product were pooled and the solvent was evaporated yielding an oil (153 mg).

GC/MS showed $M^+$ at m/e259.15 (70.9%) and the base peak at m/e=161.05. Other prominent peaks appeared at m/e=260.15 (14.2%), m/e=244.15 (32.9%), m/e=218.15 (17.3%), m/e=160.05 (29.7%), m/e=159.05 (14.9%), and m/e=110.05 (80.4%). The optical rotation was measured and was found to be $a_D^{22} = +64.9°$ (c 1.0, MeOH).

TABLE 1

Screening Data on Newly Synthesized Compounds
Effects on Dopamine (DA) and Serotonin (5-HT) Synthesis Rates
and on Motor Activity in Reserpine Pretreated Rats

| Compound | ED50 DOPA[a] stri hem (μmol/kg) | ED50 5-HTP[b] limb | Motor Act[c] | Behavior[d] | In vitro binding[e] D2 IC50 nM | 5-HT1A IC50 nM | Bioavailability[f] bioch po/sc in % | temp | plasma |
|---|---|---|---|---|---|---|---|---|---|
| 8-OMe-CPMAT[1] | | | | | | | | | |
| (sc) | P(16) I(16) | 0.40 | + | 5-HT syndr | | 6 | 12 | — | — |
| (po) | P(40) I(40) | 3.3 | + | 5-HT syndr | | | | | |
| 8-OMe-DCPMAT[2] | | | | | | | | | |
| (sc) | I(50) I(50) | 1.2 | + | 5-HT syndr | 40000 | 21 | 60 | 36 | 6–16 |
| (po) | I(50) I(50) | 2.0 | + | 5-HT syndr | | | | | |

[1]8-Methoxy-2-(N-cyclopropylmethyl-N-n-propylamino)tetralin
[2]8-Methoxy-2-(N,N-dicyclopropylmethylamino)tetralin
[a]Dose giving a half maximal decreases of DOPA formation in the rat striatal or cortical (NA predominated hemispheres) brain parts. The values were estimated from dose-response curves comprising 4 to 6 dose levels (n = 4). Maximal decrease was found to be 80% in striatum and 50% in cortex. Control levels were: striatum 3220 ng/g and cortex 150 ng/g.
[b]Dose giving a half maximal decrease of 5-HTP formation in the rat limbic brain part. The values were estimated from dose-response curves comprising 4 to 6 levels (n = 4). Maximal derease was found to be 50%. Control level was: 191 ng/g.
"P" denotes partial agonist, i.e., a submaximal decrease in DOPA or 5-HTP formation was noted at the highest dose (shown in brackets in μmol/kg) tested.
[c]Motor activity as measured in photocell-equipped motility boxes "+" and "−" denote activation and no chnage, respectively, as compared to controls (essentially no locomotion was registered in these controls (reserpinized rats)).
[d]The gross behavior of the animals was observed during the course of the experiments. The 5-HT behavioral syndrome consisted of flat body psoture, abducted hind- and forelegs, forepaw treading (piano-playing) and Straub tail.
[e]The affinity of the test compounds for dopamine D2 receptor sites was determined by calculating the IC50 value (see text).
[f]"Bioch" denotes the bioavailability as estimated by comparing the ED50 values after s.c. and p.o. administration (reserpine-pretreated rats). "Temp" denotes the bioavailabilty as estimated by comparing the decrease in rectal temperature after s.c. (25.0 μmol/kg) and p.o. (100.0 μmol/kg) administration of the test drugs in non-pretreated rats (c.f., FIGS. 1 and 2). "Plasma" denotes the availability as estimated by comparing plasma drug levels (measured by means of GC/MS) after s.c. and p.o. administration of test drugs in non-pretreated rats.

FORMULA
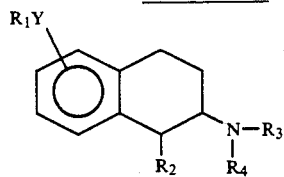
Formula I
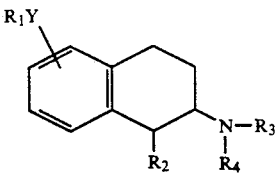
1. A compound of Formula 1 and pharmaceutically acceptable acid addition salts thereof,
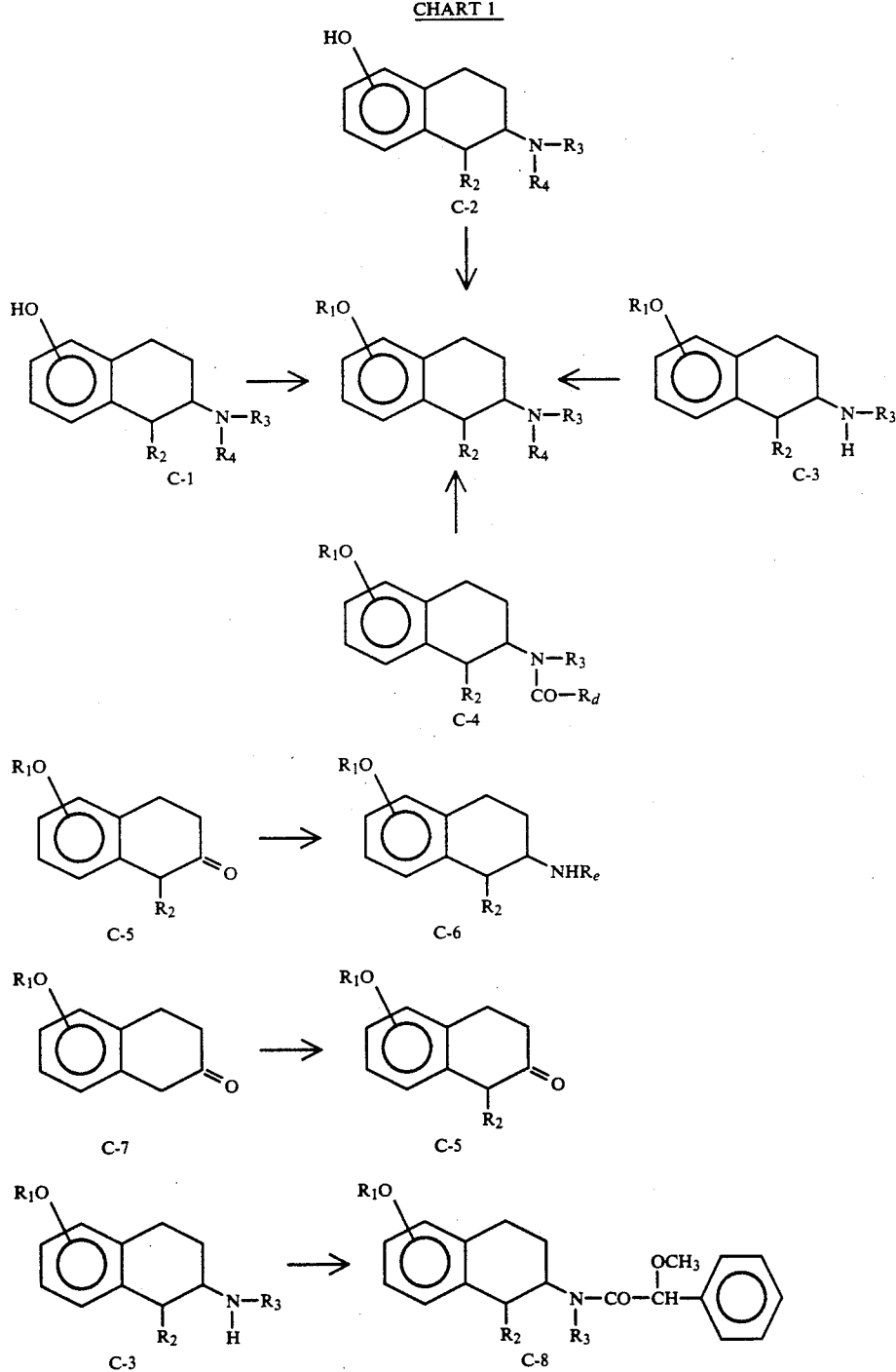
We claim:
wherein $YR_1$ is $OR_1$ at the 8 position where $R_1$ is $-CH_2-(C_{3-8}$ cycloalkyl);

$R_2$ is hydrogen or $C_{1-3}$ alkyl;

$R_3$ is $-CH_2-(C_{3-8}$ cycloalkyl);

$R_4$ is hydrogen, $C_{1-8}$ alkyl, $-CH_2-(C_{3-4}$ cycloalkyl), $-(CH_2)_3-R_5$ or $-CH_2-CH_2-X-(CH_2)_nCH_3$;

n is zero to 3

X is oxygen or sulfur; and $R_5$ is phenyl, $C_{1-3}$ alkoxy, $C_{1-3}$ alkyl, 2-thiophene, 3-thiophene, or phenyl substituted with one or two substituent groups selected from chlorine, bromine or fluorine; and with the proviso that when $R_3$ contains more than four carbon atoms and $R_4$ is alkyl, said alkyl contains from 1 to 3 carbon atoms.

2. A compound according to claim 1 wherein $R_2$ is hydrogen.

3. A compound according to claim 1 wherein $R_4$ is $C_{1-8}$ alkyl or $-CH_2-(C_{3-4}$ cycloalkyl).

4. A compound of Formula 1 and pharmaceutically acceptable acid addition salts thereof,

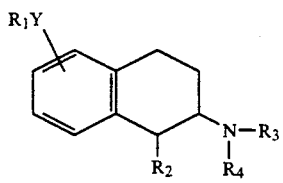

wherein
- $-YR_1$ is $-S-(C_{1-3}$ alkyl) at the 5, 6, 7 or 8 position of the aromatic ring or $OR_1$ at the 8 position where $R_1$ is selected from the group consisting of $C_{1-8}$ alkyl, $C_{2-8}$ alkenyl, $-CH_2-(C_{3-8}$ cycloalkyl) or benzyl;
- $R_2$ is hydrogen or $(C_1-C_3)$ alkyl;
- $R_3$ is $-CH_2-(C_3-C_8)$ cycloalkyl;
- $R_4$ is $-(CH_2)_m$-(2-thiophenyl or 3-thiophenyl); and m is 2 or 3.

5. A compound according to claim 4 wherein $R_2$ is hydrogen.

* * * * *